(12) United States Patent
Sanmugalingham

(10) Patent No.: US 10,803,977 B2
(45) Date of Patent: Oct. 13, 2020

(54) SYSTEM AND METHOD FOR COLLECTION, STORAGE AND MANAGEMENT OF MEDICAL DATA

(71) Applicant: SYNAPTIVE MEDICAL (BARBADOS) INC., Bridgetown (BB)

(72) Inventor: Geetha Sanmugalingham, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 15/507,414

(22) PCT Filed: Sep. 15, 2014

(86) PCT No.: PCT/IB2014/064536
§ 371 (c)(1),
(2) Date: Feb. 28, 2017

(87) PCT Pub. No.: WO2016/042356
PCT Pub. Date: Mar. 24, 2016

(65) Prior Publication Data
US 2017/0255751 A1    Sep. 7, 2017

(51) Int. Cl.
| | |
|---|---|
| *A61B 34/20* | (2016.01) |
| *G16H 10/60* | (2018.01) |
| *G06Q 50/22* | (2018.01) |
| *G06Q 10/10* | (2012.01) |
| *G06F 21/62* | (2013.01) |
| *G16H 50/70* | (2018.01) |

(Continued)

(52) U.S. Cl.
CPC ........... *G16H 10/60* (2018.01); *A61B 34/20* (2016.02); *G06F 21/6254* (2013.01); *G06Q 10/10* (2013.01); *G06Q 50/22* (2013.01); *A61B 2090/103* (2016.02); *G06F 19/321* (2013.01); *G16H 50/70* (2018.01)

(58) Field of Classification Search
USPC ....................................................... 705/2–4
See application file for complete search history.

(56) References Cited

U.S. PATENT DOCUMENTS 7,865,376 B2 * 1/2011 Ober .................. G06F 19/322
705/2
2002/0052761 A1    5/2002 Fey
(Continued)

OTHER PUBLICATIONS

Ralston, James D., et al. "Patient web services integrated with a shared medical record: patient use and satisfaction." Journal of the American Medical Informatics Association 14.6 (2007): 798-806.*

(Continued)

*Primary Examiner* — Mark Holcomb

(57) ABSTRACT

The present invention provides a method and system for storing and accessing medical records. The method includes anonymizing patient records, aggregating and analyzing the records, and storing the results of the analysis in a health informatics database. The system includes a database with patient records, a processor for anonymizing the patient records, a second database with anonymized patient records, an interface to access the second database, analyze the records and store the results, an output to display the results and a health informatics database to store the correlated record.

18 Claims, 9 Drawing Sheets

(51) Int. Cl.
    *G06F 19/00*     (2018.01)
    *A61B 90/10*     (2016.01)

(56) References Cited

U.S. PATENT DOCUMENTS

| | | | |
|---|---|---|---|
| 2002/0123905 A1* | 9/2002 | Goodroe | G06F 19/325 705/2 |
| 2004/0122705 A1* | 6/2004 | Sabol | G06F 19/324 705/2 |
| 2008/0147554 A1 | 6/2008 | Stevens et al. | |
| 2008/0177576 A1* | 7/2008 | Jennings | G06F 19/322 705/3 |
| 2010/0042429 A1* | 2/2010 | Dixit | G06Q 50/22 705/2 |
| 2010/0070300 A1* | 3/2010 | Anderson | G06Q 10/10 705/2 |

OTHER PUBLICATIONS

Pace et al., "Database Design to Ensure Anonymous Study of Medical Errors: A Report from the ASIPS Collaboration", Journal of the American Medical Informatics Association, Nov./Dec. 2003, vol. 10, No. 6, pp. 531-540.

Scott, Anne Marie, "International Search Report, PCT Application No. PCT/IB2014/064536" dated May 28, 2015.

* cited by examiner

SYSTEM AND METHOD FOR COLLECTION, STORAGE AND MANAGEMENT OF MEDICAL DATA

FIELD

The present disclosure relates to methods for storing and accessing medical records, and more specifically relates to methods and systems for anonymizing, aggregating and analyzing patient records.

BACKGROUND

The health-care industries throughout the world consist of various systems of health-care management and treatment, from private health-care services to public, state-based and nationalised health-care systems to a combination of these systems at regional levels. The variety of service structures available to patients leads to several different methods of collection of health-related data, which may affect the availability of such data to researchers and administrative officials. Furthermore, the diversity of information in medical records, ranging from text-based descriptions to medical imaging, results in fragmented information that is difficult to analyze in aggregate.

In the U.S., the combination of data-management systems, laws around confidentiality and access with respect to patient-related health data leads to difficulty in using data collected from patients to facilitate relevant and crucial research projects, and to develop policies and procedures for effective and innovative population-based health issues.

Canada's public patient health-record management systems are designed with two goals in mind: to provide researchers with relevant patient data for medical research purposes, and to aid administrators in the development of effective population-based health policies. Both of these aims facilitate the progress of an integrated, interactive and intuitive health-care system that is built on the efficient allocation of research and policy resources. The advantages that a public system of health-records collection and management provides include an understanding of surgical waiting lists, the utilization of resources by those with a specific health problem, and understanding the relationship between drug utilization and patient use of other health interventions.

Further, the data collected in public health care systems can be used to develop health-care management policies for populations, trace health-trends in populations and to address issues of ethics, confidentiality and long-term health of individuals and populations. Using the method of individual data sets to infer health trends for populations has long been an important factor in effective health resource management.

Jurisdictions with nationalised health-care systems typically have methods in place to systematically collect and store patient information at the national, regional and provincial levels. However, the lack of aggregate data collection systems in the health-care field is problematic for jurisdictions without public health care, such as the U.S. In the U.S., such a central data-collection and management system does not exist due to the lack of a centralised health-care system, the existence of private health-care providers, state-level health-care management policies that do not provide reciprocity in exchanging of patient information and health records and the existence of privacy laws that prevent the collection of health-related data for the purposes of the creation of population-based healthcare policies.

In Canada, the current linked health data collection, storage and management systems divide patient information into six types of files which are arranged according to the information collected on individual patients through the health care system. These six types are: medical services, hospital separations, drug prescriptions for the elderly, long term care services, deaths and births. The current system is currently undergoing linkage based on a methodology that focuses on developing an aggregate system of data collection.

One problem with this system is the existence of "grey areas" in the links, which lead to the possibility of false positives and bad links being developed, potentially misleading research trends, obfuscating methodologies and creating skewed results. Another problem with the current system is that it does not allow for data exchange across different systems, as would be the case if the Canadian health care data management systems were to be applied to the mix of public-private systems in the U.S., in their current state.

What is lacking is a resource that stores patient records including diverse information such as symptoms presentation, diagnosis, medical interventions, outcomes, costs, payers and reimbursement and that links details of all these aspects of patient records together in an anonymized and accessible database. Further lacking is such a comprehensive database that can also be searched and analyzed by researchers, medical personnel and administrators to provide information and statistics that enable decisions for optimum patient care, hospital administrative planning and budgeting.

SUMMARY

An object of the present invention is to provide systems and methods for data collection, storage and management that anonymizes and aggregates patient records, and permits the aggregated patient records to be analyzed while maintaining privacy and ethical considerations.

Thus by one broad aspect of the present invention, a method is provided for receiving a record within a first dataset, each record including a plurality of identification fields, which when combined collectively, uniquely identify an individual, and an at least one health care field corresponding to health care data associated with the individual; associating a unique identifier with the identification fields in the record; storing an anonymized record within a second dataset, each anonymized record in the second dataset comprising the heath care fields and the associated unique identifier from the record in the first dataset; classifying and analyzing the anonymized record based on at least one of the health care fields; storing an output of the analysis as a correlated record in a health informatics database; and displaying the output of the analysis on an output interface.

By another broad aspect of the present invention, a system is provided to store and access medical information comprising a database for storing a patient record, each record including a plurality of identification fields, which when combined collectively, identify an individual, and at least one health care field corresponding to health care data associated with the individual; a second database; a processor in communication with the first and second database for performing the steps of selecting a record from the first database, assigning a unique identifier based on the plurality of identification fields, and storing in a second record in the second database the unique identifier as well as the at least one health care field from the selected record of the first database; an interface for accessing the second database, the interface being operable to retrieve records from the second database, classify and analyze the records according to at least one health care field, store the analysis as a correlated record in a health informatics database and output the correlated record to an output interface; an output interface to receive the correlated record from the interface; and a health informatics database to store the correlated record.

BRIEF DESCRIPTION OF THE DRAWINGS

Embodiments will now be described, by way of example only, with reference to the drawings, in which.

DETAILED DESCRIPTION

Figure 1:
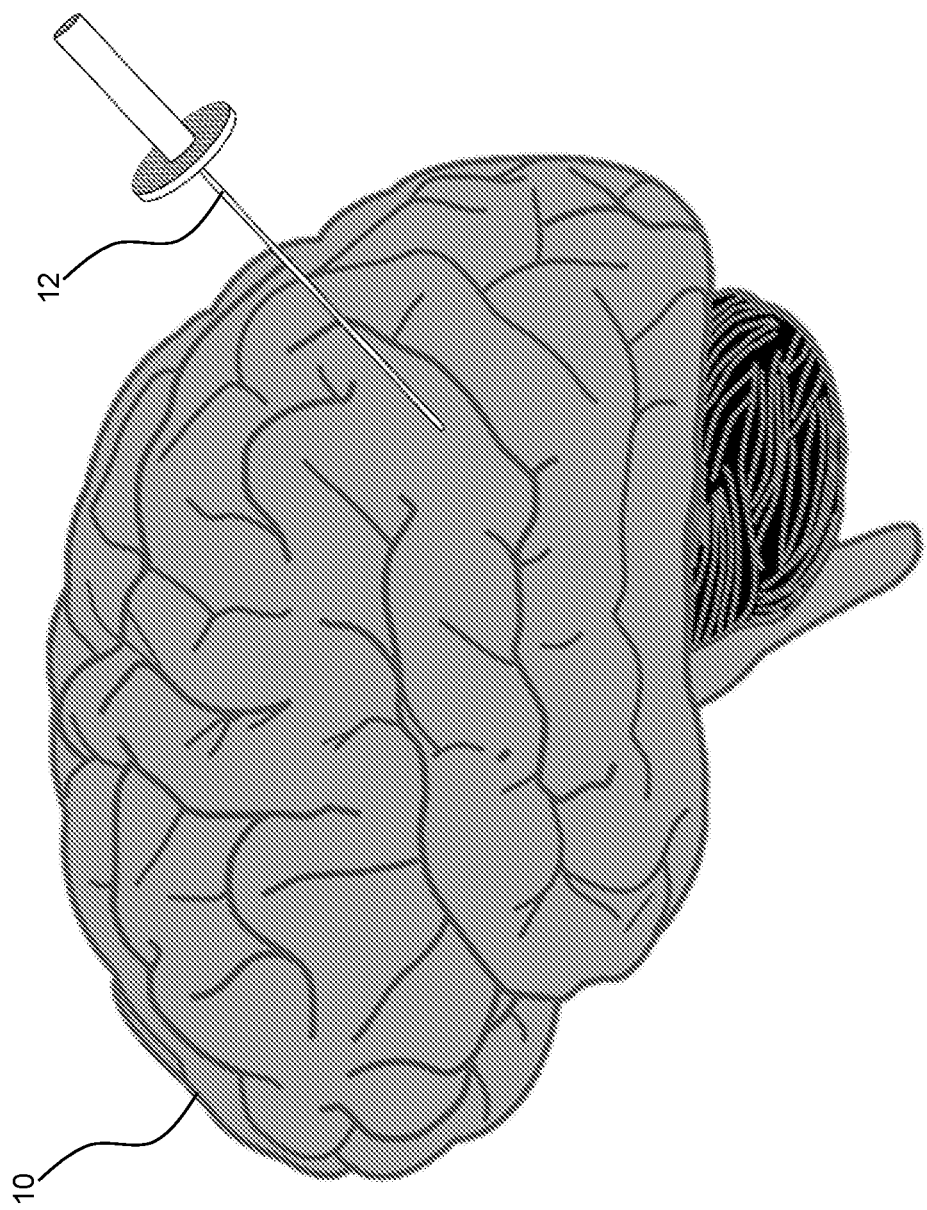
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings.

It is noted that the phrase "outcome", as used herein, refers to quantifiable methods to measure mortality and morbidity of the subject. This includes, but is not limited to, measurement of actual patient function, including direct measures of tissue viability, or higher-level function, as well as indirect measurements, tests and observations. An outcome may also refer to the economic outcome of a procedure (in a specific or broad sense), and may include the time for the procedure, the equipment and personal utilization, drug and disposable utilization, length of stay, and indications of complications and/or comorbidities.

In some examples, the present disclosure may enable better sharing of information across separate data sources within a given health system, as well as across separate health systems.

In some examples, the present disclosure may help to integrate information from separate health systems and/or help to communicate information across separate health systems, such as health-care management systems from separate regions or countries.

While some embodiments of the present disclosure can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

Example embodiments of the present disclosure will be described with reference to neurology and neurosurgery procedures to provide an illustration of medical data that may be maintained for a given patient and used for analysis in an anonymized and aggregated format, as illustrated by the figures described below.

Prior, during and following a neurosurgical procedure, medical data is collected. The data may be utilized in planning surgery and for navigation during surgery. As data is accumulated, it may be used to plan subsequent neurosurgical procedures for the same or other patients, within the same hospital setting or a different hospital. The data may also be utilized for other aspects of medical care, for example to indicate possible tumor type, optimal follow-up procedures and resources the hospital may require regarding hospital personnel and patient stay requirements. A description of a neurosurgical procedure and associated data collection and use is provided below.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO BrainPath™. Surgical tools and instruments may then be inserted within the lumen of the access port 12 in order to perform surgical, diagnostic or therapeutic procedures, such as resecting tumors as necessary. In some examples, the present disclosure may apply equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain 10. Surgical instruments would then be inserted down the access port 12.

Optical tracking systems, used in the medical procedure, may track the position of a part of the instrument that is within line-of-site of the optical tracking camera. These optical tracking systems also typically require a reference to the patient to know where the instrument is relative to the target (e.g., a tumor) of the medical procedure. These optical tracking systems typically require a knowledge of the dimensions of the instrument being tracked so that, for example, the optical tracking system is able to determine the position in space of a tip of a medical instrument relative to the tracking markers being tracked.

Figure 2:
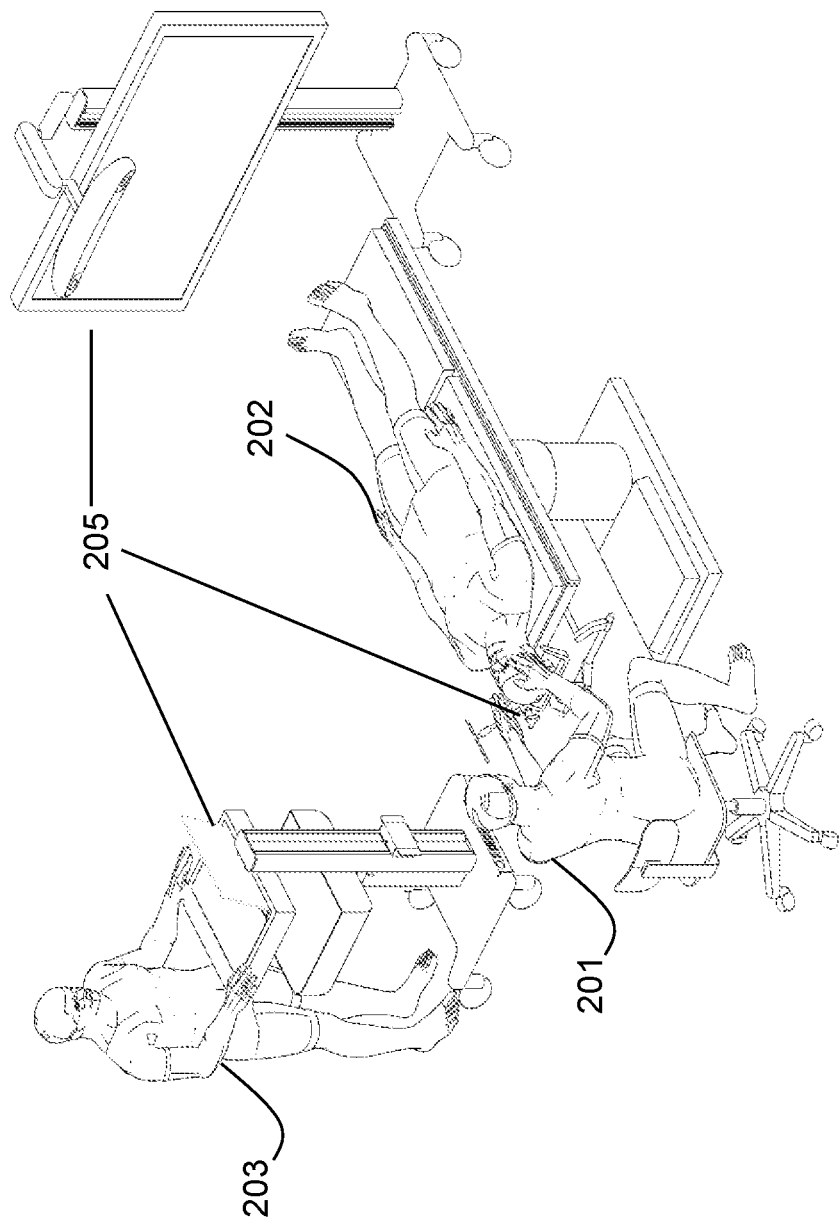
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. An example medical navigation system 205 comprising an equipment tower, tracking system, display(s) and tracked instrument(s) assist the surgeon 201 during his procedure. An operator 203 may also be present to operate, control and provide assistance for the medical navigation system 205.

Figure 3:
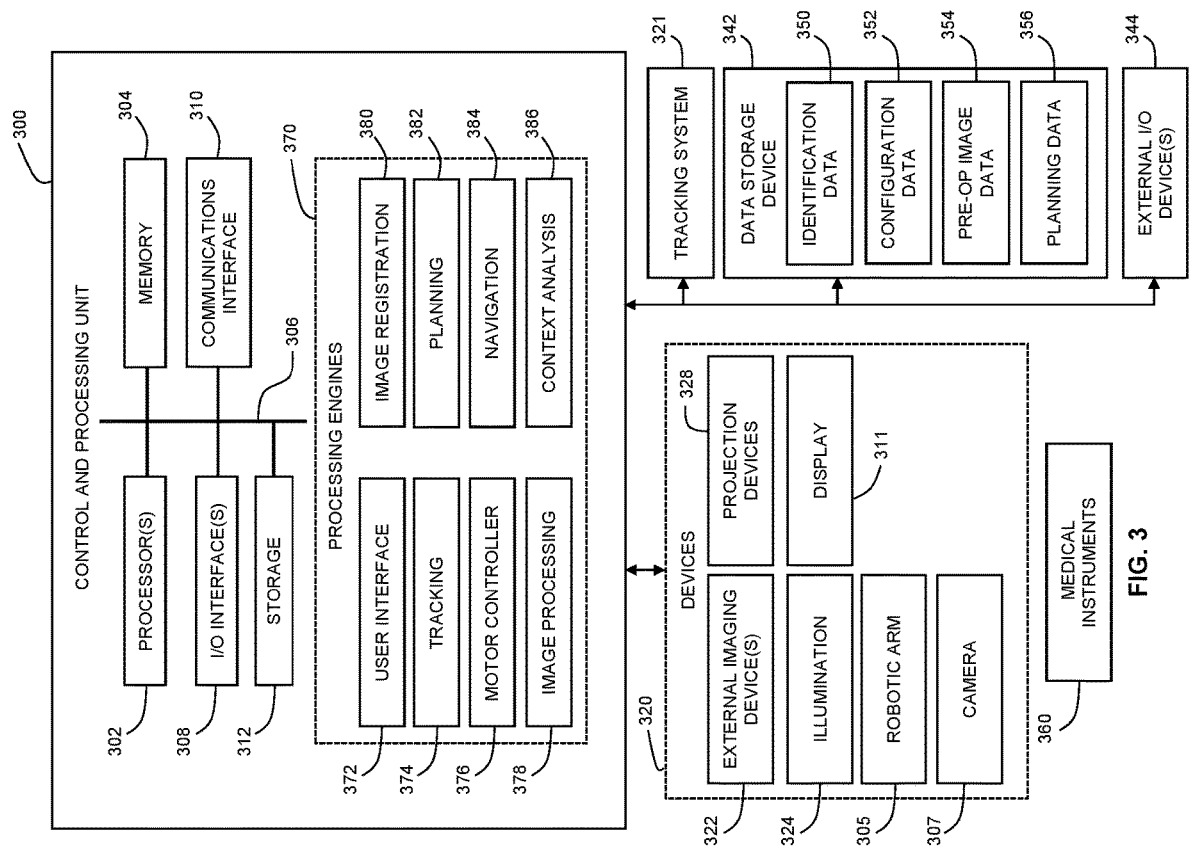
FIG. 3 is a block diagram illustrating a control and processing system that may be used in the navigation system shown in FIG. 2.

Referring to FIG. 3, a block diagram is shown illustrating an example control and processing system 300 that may be used in the medical navigation system 205 shown in FIG. 2 (e.g., as part of the equipment tower). As shown in FIG. 3, in one example, control and processing system 300 may include one or more processors 302, an internal and/or external memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 may be identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intra-operative reference frame. For example, medical instruments 360 may include tracking markers such as tracking spheres that may be recognizable by a tracking camera 307. In one example, the tracking camera 307 may be an infrared (IR) tracking camera. In another example, a sheath placed over a medical instrument 360 may be connected to and controlled by control and processing unit 300.

Control and processing unit 300 may also interface with a number of configurable devices, and may intra-operatively reconfigure one or more of such devices based on configuration parameters obtained from configuration data 352. Examples of devices 320, as shown in FIG. 3, include one or more external imaging devices 322, one or more illumination devices 324, a robotic arm, the tracking camera 307, one or more projection devices 328, and one or more displays 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

In some examples, the control and processing system 300 may include one or more interfaces, such as communications interface 310, for communicating with an informatics system. One or more processing modules or engines 370, such as the procedure planning engine 382 and the user interface engine 372, may receive data communicated from an informatics system and may use such data in its processing prior to, during, or after an operation, for example. The control and processing system 300 may also communicate data, such as image data from image processing engine 378, to an informatics system.

It is to be understood that the control and processing system 300 is not intended to be limited to the components shown in FIG. 3. For example, one or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
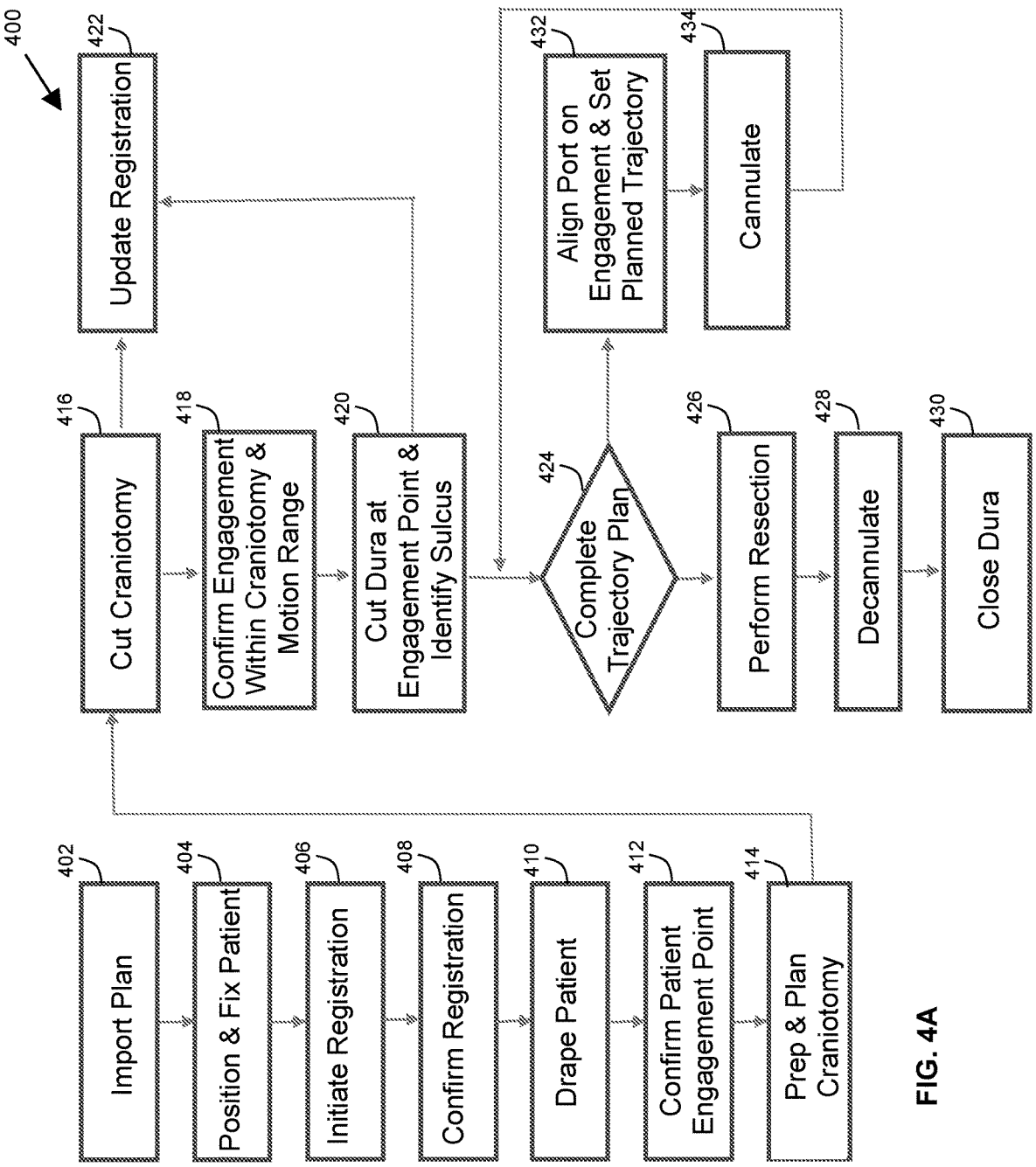
FIG. 4A is a flow chart illustrating a method involved in a surgical procedure using the navigation system of FIG. 2.

Referring to FIG. 4A, a flow chart is shown illustrating an example method 400 of performing a port-based surgical procedure using a navigation system, such as the medical navigation system 205 described in relation to FIG. 2. At a first block 402, the port-based surgical plan is imported. An example of the process to create and select a surgical plan is outlined in International Patent Application No. CA/2014/050272 titled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entireties.

Once the plan has been imported into the navigation system at the block 402, the patient is affixed into position using a body holding mechanism. The head position is also confirmed with the patient plan in the navigation system (block 404), which in one example may be implemented by the computer or controller forming part of the navigation system 205.

Next, registration of the patient is initiated (block 406). The phrase "registration" or "image registration" refers to the process of transforming different sets of data into one common coordinate system. Data may include multiple images (e.g., still photographs or videos), data from different sensors, times, depths, or viewpoints. The process of "registration" is used in the present application to refer to medical imaging in which images from different imaging modalities are co-registered. The navigation system may define a three-dimensional virtual space within which images may be registered, as described further below. Registration may be used in order to be able to compare or integrate the data obtained from these different modalities, for example.

Those skilled in the relevant arts will appreciate that other registration techniques may be suitable and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods typically are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
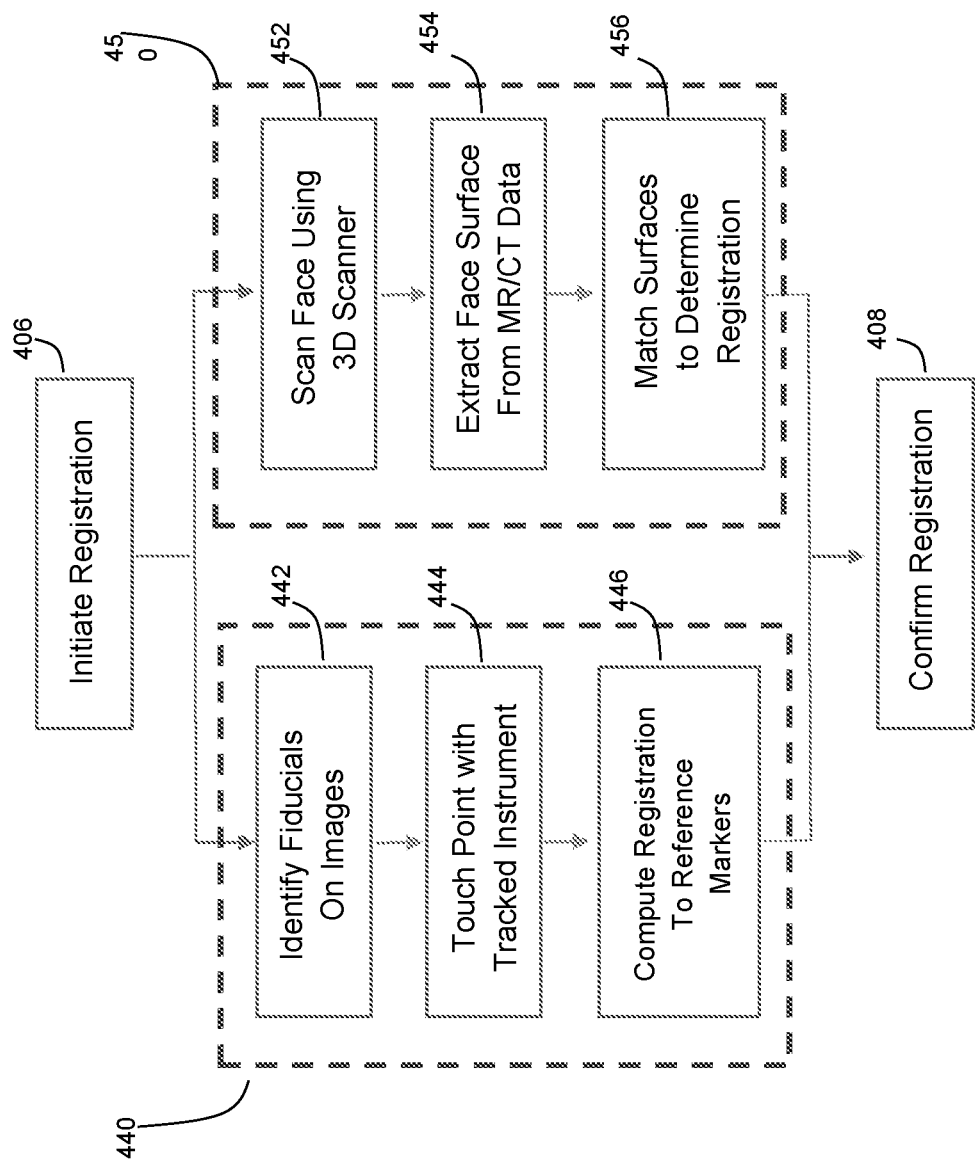
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. Block 440 illustrates an approach using fiducial touch points, while block 450 illustrates an approach using a surface scan. The block 450 is not typically used when fiducial touch points or a fiducial pointer is used.

If the use of fiducial touch points (block 440) is contemplated, then the method may involve first identifying fiducials on images (block 442), then touching the touch points with a tracked instrument (block 444). Next, the navigation system computes the registration to reference markers (block 446).

Alternately, registration can be completed by conducting a surface scan procedure (block 450). In this approach, the patient's head (e.g., face, back of head and/or skull) may be scanned using a 3D scanner (block 452). Next, the corresponding surface of the patient's head is extracted from pre-operative image data, such as MR or CT data (block 454). Finally, the scanned surface and the extracted surface are matched to each other to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas.

At this point, conventional navigation systems typically require that the non-sterile patient reference is replaced with a sterile patient reference of identical geometry location and orientation. Numerous mechanical methods may be used to minimize the displacement of the new sterile patient reference relative to the non-sterile one that was used for registration but it is expected that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414). Planning the procedure may involve retrieving an existing partially-prepared treatment plan that may have been prepared based on the patient's pre-operative data. Planning the procedure may be aided by information from an informatics system. Intra-operative data, such as the registered image of the patient's actual skull surface, may be used to adjust an existing partially-prepared treatment plan, for example.

Upon completion of the preparation and planning of the craniotomy, the craniotomy is cut and a bone flap is temporarily removed from the skull to access the brain (block 416). In some examples, cutting the craniotomy may be assisted by a visual indication of the location, size and/or shape of the planned craniotomy (e.g., a projection of a planned outline onto the patient's skull). Registration data may be updated with the navigation system at this point (block 422), as appropriate.

Next, the engagement within craniotomy and the motion range are confirmed (block 418). Next, the procedure advances to cutting the dura at the engagement points and identifying the sulcus (block 420). Registration data may again be updated with the navigation system at this point (block 422).

In some examples, by focusing the camera's view on the surgical area of interest, update of the registration data (block 422) may be adjusted to help achieve a better match for the region of interest, while ignoring any non-uniform tissue deformation, for example, affecting areas outside of the region of interest. Additionally, by matching image overlay representations of tissue with an actual view of the tissue of interest, the particular tissue representation may be matched to the live video image, which may help to improve registration of the tissue of interest. For example, the registration may enable: matching a live video of the post craniotomy brain (with the brain exposed) with an imaged sulcal map; matching the position of exposed vessels in a live video with image segmentation of vessels; matching the position of lesion or tumor in a live video with image segmentation of the lesion and/or tumor; and/or matching a video image from endoscopy up the nasal cavity with bone rendering of bone surface on nasal cavity for endonasal alignment.

In some examples, multiple cameras can be used and overlaid with tracked instrument(s) views, which may allow multiple views of the image data and overlays to be presented at the same time. This may help to provide greater confidence in registration, or may enable easier detection of registration errors and their subsequent correction.

Thereafter, the cannulation process is initiated. Cannulation typically involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

In some examples, the cannulation process may also support multi-point trajectories where a target (e.g., a tumor) may be accessed by cannulating to intermediate points, then adjusting the cannulation angle to get to the next point in a planned trajectory. This multi-point trajectory may be contrasted with straight-line trajectories where the target may be accessed by cannulating along a straight path directly towards the target. The multi-point trajectory may allow a cannulation trajectory to skirt around tissue that the surgeon may want to preserve. Navigating multi-point trajectories may be accomplished by physically reorienting (e.g., adjusting the angle of) a straight access port at different points along a planned path, or by using a flexible port, such as an access port with manipulatable bends that may be bent along the multi-point trajectory.

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIGS. 4A and 4B may be specific to port-based surgery, such as portions of blocks 428, 420, and 434, but the appropriate portions of these blocks may be skipped or suitably modified when performing non-port-based surgery.

When performing a surgical procedure using a medical navigation system 205, as outlined in connection with FIGS. 4A and 4B, the medical navigation system 205 typically must acquire and maintain a reference of the location of the tools in use as well as the patient in three dimensional (3D) space. In other words, during a navigated neurosurgery, there typically needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative images (e.g., MRI or CT imagery) to the physical space of the surgery, such as the patient's head. This may be accomplished by the navigation system 205 tracking locations of fiducial markers fixed to the patient's head, relative to the static patient reference frame. The patient reference frame is typically rigidly attached to the head fixation device, such as a Mayfield™ clamp. Registration is typically performed before the sterile field has been established (e.g., the step 410 shown in FIG. 4A).

Figure 5A:
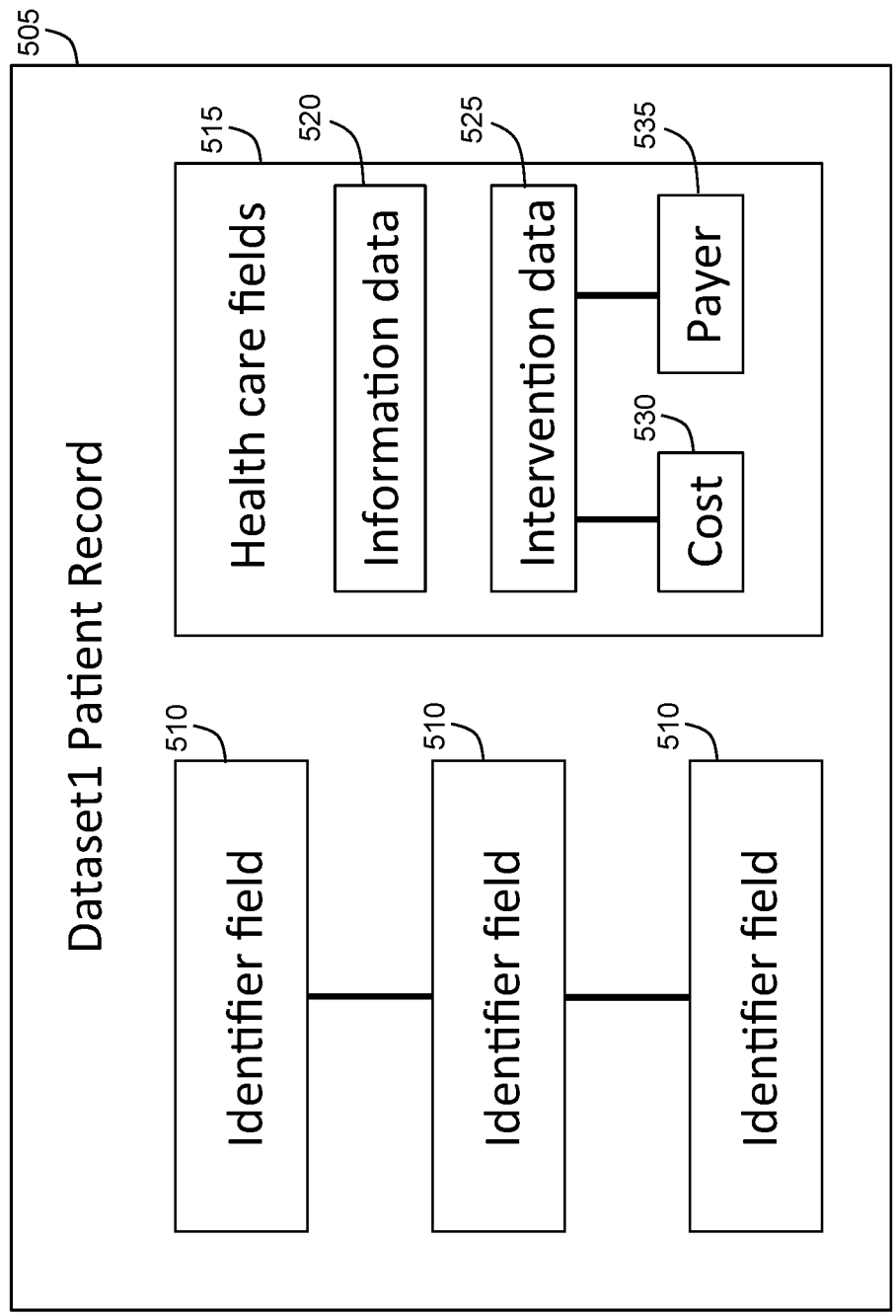
FIG. 5a illustrates a patient Dataset1 with patient identifier and health care fields.
Figure 5B:
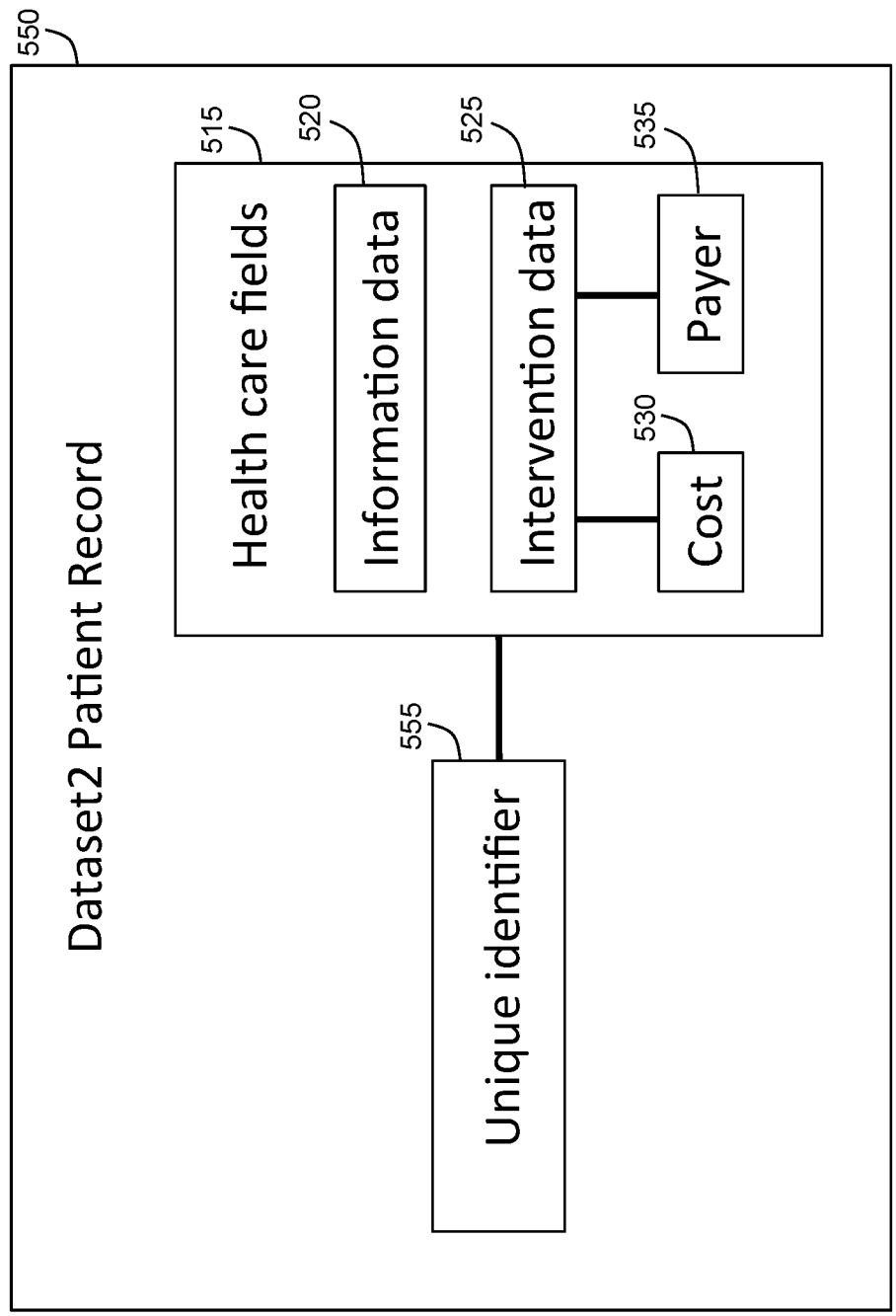
FIG. 5b illustrates a patient Dataset2, in which the records are anonymized.

A system and method for collection, storage and management of a medical database is now described. FIGS. 5A and 5B illustrate an example medical database, as disclosed herein.

As shown in FIG. 5A, patient records are received in a Dataset1 505. The patient records stored in Dataset1 include multiple patient identifier fields 510 that uniquely identify an individual and one or more health care fields 515. The health care fields 515 are data that relate the medical records of the individual. The health care fields 515 may include two types of data: information data 520 and intervention data 525. Information data 520 includes details such as for example patient symptoms, identification of the medical professional treating the individual, the hospital or other institute, and geographical location. Information data 520 is data that is not associated with a cost. Intervention data 525 includes details on treatment of the patient, such as for example medical examinations, pharmaceutical prescriptions, clinical tests, diagnosis, imaging data (eg MRI, CT, ultrasound) surgery, physiotherapy, clinical outcome, hospital admittance, etc. Intervention data 525 relates events that have a cost, therefore Intervention data may be associated with a cost code 530 and a payer code 535. A patient record in Dataset1 505 may include or integrate existing hospital records, and the health care fields 515 may be in multiple formats.

Once a patient record is entered in the Dataset1 505, additional health care fields 515 may be received for that patient at a later time by using the patient identifier fields 510 to match the new health care data to the individual. Thus the patient records may be longitudinal medical records for that individual by storing multiple health care records and linking them to the unique identifier fields.

Although not specifically indicated, it should be understood that such communication may be two-way, may be wired or wireless communication (e.g., via wired or wireless networks, such as via an intranet or via the Internet), may be via removable and fixed media, and may take place over secure communication channels.

As illustrated in FIG. 5B, each patient record in Dataset1 505 is anonymized and stored in a Dataset2 550 such that the record cannot be associated with any individual patient. One example method to anonymize the patient records is to assign a unique identifier 555 to a patient record in Dataset1 505, and then store the unique identifier 555 and the associated health care fields 515 in Dataset2 550, without the patient identifier fields 510. For example, the unique identifier may be assigned based on the name and birth date in the identification fields 510.

Dataset2 550 is a collection of anonymized patient records that can be accessed by parties such as researchers, medical professionals and hospital administrators, without infringing privacy regulations. Dataset2 550 is a valuable asset for researchers and administrators to evaluate optimal treatment options, cost effectiveness of treatments and trends for future medical requirements. Access to Dataset2 550 may be provided to researchers or administrators, for example by transmitting it or parts of it to a local or remote interface.

Each record in Dataset2 550 is stored in a hierarchical structure, in which the health care fields 515 are linked to the unique identifier 555 and layers of information are stored. For example, the intervention fields 525 may be linked with a cost code 530 and payer code 535. Furthermore, image data, such as MRI or CT scan images, may be linked or overlaid with text.

Figure 6:
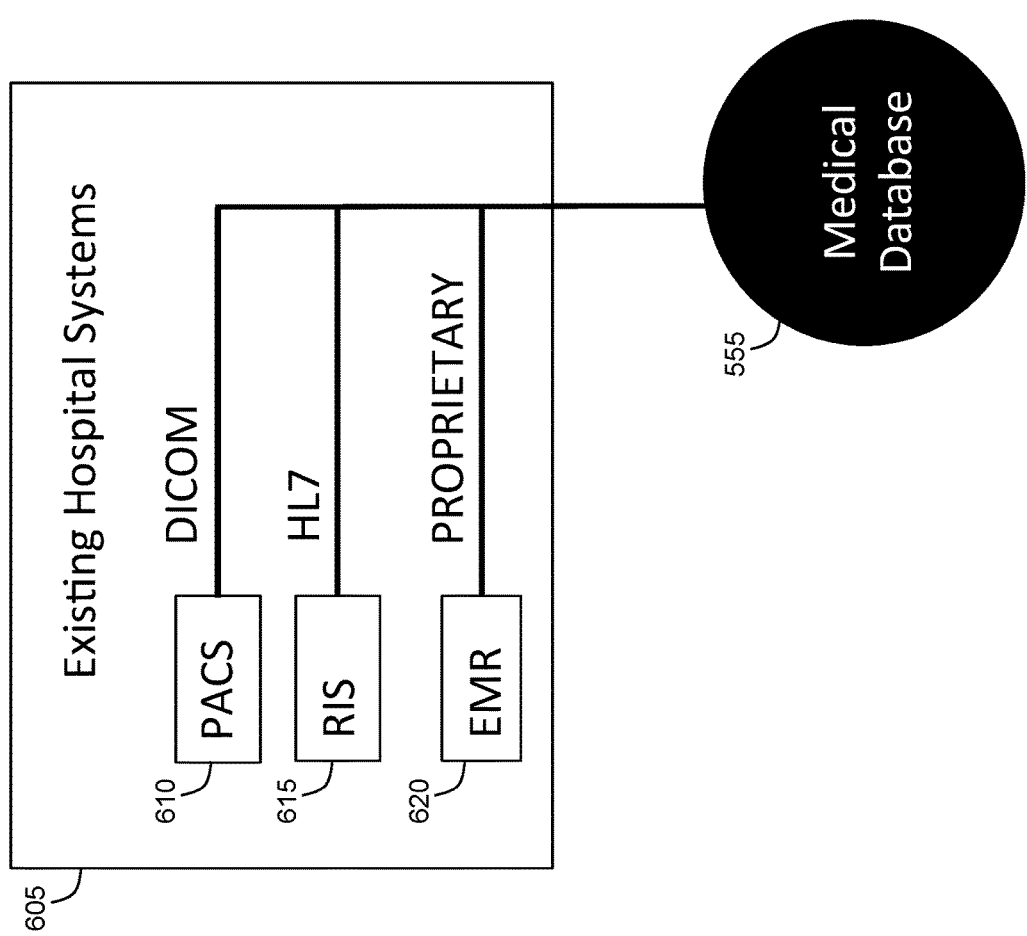
FIG. 6 is a diagram showing examples of data formats for health care fields in the medical database.

As illustrated in FIG. 6, existing hospital records 605 may include databases such as picture archiving and communication system (PACS) 610, radiology information system (RIS) 615 and electronic medical records (EMR) 620. The EMR or other databases of the hospital system may store information specific to a given patient treatment, such as the pathology treated, the treatment plan used, lab testing carried out, and the treatment outcome, for example. The databases in the hospital system may communicate data each in a different format. For example, PACS 610 may store only DICOM images, RIS 615 may store data according to the HL7 standard, and EMR 620 may store data in the hospital's own proprietary format. The data communicated to/from the medical database may be of any suitable format, and the output may include modules or plug-ins to translate data formats for transmission to any given database.

Figure 7:
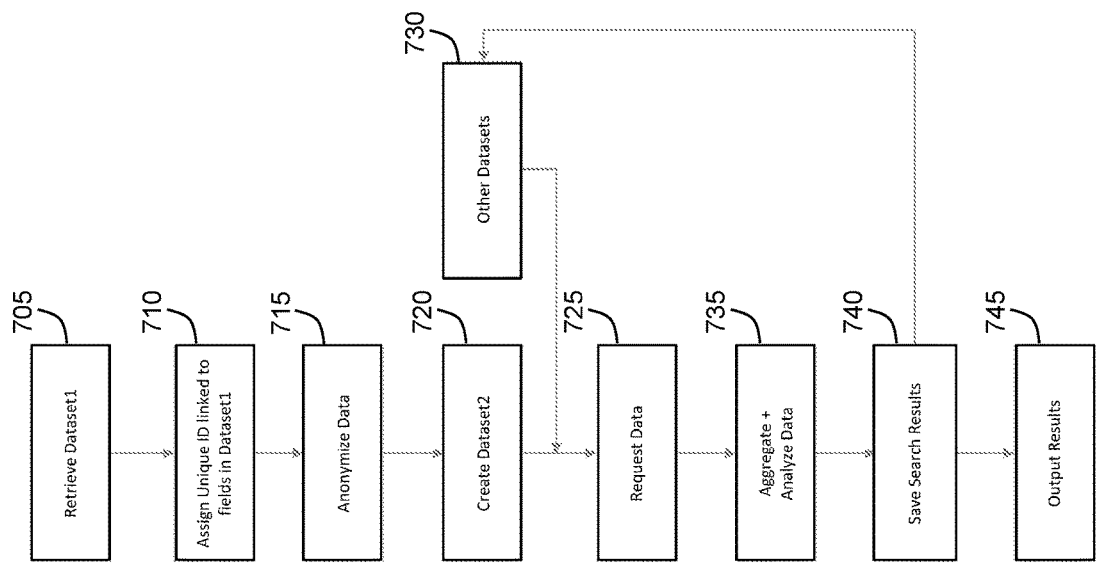
FIG. 7 is a flow chart illustrating a method of receiving, anonymizing, aggregating and analyzing patient records.

As further illustrated in FIG. 7, Dataset1 is retrieved 705, the patient records in Dataset1 are assigned a unique identifier 710 which is used to anonymize the data 715, and the anonymized data is used to create Dataset2 720. The data is requested from Dataset2 725. Other data sets 730 may be integrated with Dataset2 720 or evaluated separately. The interface to provide data from other datasets 730 may have additional processors and memory stores that map the data fields of the other datasets 730 to the corresponding data fields of Dataset2 720. This supports integration of the data of the two systems with no loss of data or function. Integration of other datasets 730 advantageously provides a doctor with a more comprehensive medical report and provides a clearer picture of the health of the patient while reducing time and cost of deploying two disparate information systems. The other datasets 730 may also be multi-hospital or multi-site.

Dataset2 720 may push data to other datasets 730, and may provide data to other datasets in response to requests. Similarly, Dataset2 720 may query (or pull) other datasets 730 for information, and other datasets 730 may transmit data to Dataset2 720 without an explicit query. In some examples, Dataset2 720 may not receive a copy of the data, but rather may simply reference data that resides in other datasets 730, which may be useful to reduce bandwidth usage. Referencing data may help avoid data duplication and re-entry. Such communication of data to/from Dataset2 720 may provide a rich set of data for analysis 735 as described further below.

The records in Dataset2 720 and, if included, other datasets 730, are aggregated and analyzed 735. The aggregation and analysis 735 of the data may be accomplished by searching the health care fields for a particular value, for example a particular diagnostic code, surgery, or hospital site and saving the results of the search 740 to a health informatics database. The search may be carried out using a search engine such as Apache Lucene, to provide cross-platform searching, multiple query types, fielded searching and the capability to sort results by any field.

The search results 740 provide a set of correlated medical records from Dataset2 which are saved in a health informatics database and which may then be sorted according to values for health care fields. The search results may be searched further for values in other health care fields and the result of the second search is also saved. For example, searches of interest may include a particular surgical procedure and long-term outcome, length of hospital stay and incidence of re-admission to hospital, hospital sites and incidence of mortality, or a particular procedure and associated costs. Analysis of the search results may include determination of correlations between values for two different health care fields.

In some examples, the analysis may provide the user with recommended treatment parameters (e.g., based on relevant historical treatment parameters that are associated with positive patient outcomes). In other examples, the analysis may simply be informative in nature, for example by filtering out historical data to only present the user with the most relevant historical treatment parameters (e.g., filtering according to the specific treatment type and/or treatment stage, filtering according to the specific patient or patient type) or by providing the user with a mapping of historical treatment parameters for different treatment target locations, without providing any recommendations.

The results of the analysis or data search 740 may be presented 745 on a remote device, such as a tablet, smartphone, computer, etc. using a graphical interface. Any suitable processing and/or data presentation modules and/or plug-ins may be implemented, and modules and/or plug-ins may be updated, added or removed dynamically. Certain modules that are considered clinically relevant in a certain medical context may be provided for that medical context. For example, a neurosurgical analysis may include modules and plug-ins for managing and interpreting pre-, intra-, and post-operative imaging data across multiple patients and procedures. Likewise, modules that are relevant for hospital administration may include modules and plug-ins for predicting trends in patient needs and resource planning.

In an example of a preferred embodiment, a hospital administrator may be interested in understanding where the burden of his/her length of stay costs are in glioma patients in neurosurgery for the year 2014. The administrator searches the anonymized Dataset2 for all glioma patients in 2014, using the glioma Diagnosis code and the year of 2014 as search parameters. The administrator then analyzes the search results for health care field values that correlate with length of hospital stay and finds older patients tend to have longer stays. Based on this trend, the administrator implements certain protocols to combat the length of stay issue with the hospital staff. The correlated records are saved in the health informatics database and after a year, the administrator is interested in understanding if the protocols have initiated change to the older patients at the hospital. The administrator would search and age-adjust for glioma patients in the year 2015, and analyze whether there remains a trend for longer hospital stays for older patients. The results for the year 2015 can be compared to the saved correlated records from the year 2014 in order to assess that the protocols are indeed making a difference in patients' length of stay and in the costs.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A computer-implemented method for storing and accessing medical records to relate health care data with health care costs and normalize health care costs, comprising:

receiving at least one first record within a first dataset, each at least one first record comprising a plurality of identification fields which, when collectively combined, uniquely identify an individual and a plurality of health care fields corresponding to health care data associated with the individual, the plurality of health care fields comprising an information field and an intervention field associated with at least one of a cost field and a payer field, receiving comprising receiving the information field comprising a diagnosis code, and receiving comprising receiving the intervention field comprising a procedure code;

associating a unique identifier with the plurality of identification fields in the at least one first record;

storing at least one anonymized record within a second dataset, each at least one anonymized record in the second dataset corresponding to the plurality of health care fields and the associated unique identifier from the at least one first record in the first dataset;

interfacing the second dataset with a plurality of third records from a third dataset by using a processor, interfacing comprising mapping a plurality of health care fields from the third dataset to the plurality of health care fields of the second data set, thereby integrating the plurality of third records from the third dataset with the at least one anonymized record of the second dataset, and thereby forming a combined dataset;

analyzing the at least one anonymized record in the combined dataset using a first health care field and a second health care field of the plurality of health care fields, wherein the second health care field comprises the intervention health care field;

analyzing the first health care field and the second health care field in the combined dataset, analyzing the first health care field and the second health care field comprising filtering historical data according to a specific treatment type and a treatment stage, thereby providing an output of an analysis;

storing the output in a health informatics database;

displaying the output on an output interface, displaying comprising translating the output into at least one data format, displaying comprising overlaying data from a first health care field on data from a second health care field; and modifying a health care practice to reduce correlation between the first health care field and the second health care field, thereby normalizing health care costs.

2. The method according to claim 1, wherein receiving comprises receiving a health care field of the plurality of health care fields and linking the health care field to an existing first record in the first dataset by using the plurality of identification fields.

3. The method according to claim 1, wherein receiving comprises receiving the plurality of health care fields in a format comprising at least one data type of: DICOM, Non-DICOM, Video, Portable Document Format (PDF), Extensible Markup Language (XML), Audio, Image, and Text.

4. The method according to claim 1, wherein receiving further comprises receiving the information field comprising at least one of: an institution, a geographical location, physician identification; at least one symptom, disease code, tumour pathology code, short-term outcome, long-term outcome; hospital admission, and hospital discharge code.

5. The method according to claim 1, wherein receiving further comprises receiving the intervention field comprising at least one of: a length of hospital stay, a pharmaceutical claim, a laboratory test code, surgical information, a radiology procedure, and a rehabilitation procedure.

6. The method according to claim 1, wherein analyzing the anonymized record comprises searching the combined dataset for at least one combined record with a specified value in at least one health care field of the plurality of health care fields.

7. The method according to claim 1, wherein storing comprises storing the output of the analysis as a group of selected medical records.

8. The method according to claim 1, wherein storing comprises storing the health informatics database on at least one of: a local server, a cloud-based storage system, and a remote device.

9. The method according to claim 1,
wherein displaying comprises displaying the combined data on the output interface.

10. The method according to claim 1, wherein interfacing comprises transmitting the anonymized data to a remote interface for analysis.

11. A system for storing and accessing medical information comprising:

a first database for storing a plurality of records, each record comprising a plurality of identification fields which, when collectively combined, identify an individual and a plurality of health care fields corresponding to health care data associated with the individual, the plurality of health care fields comprising an information field and an intervention field associated with at least one of a cost field and a payer field, the information field comprising a diagnosis code, and the intervention field comprising a procedure code;

a second database;

a first processor in communication with the first database and the second database, the processor configured to: select a first record from the first database, whereby a selected first record is provided; assign a unique identifier to the first record based on the plurality of identification fields; and store the unique identifier and the plurality of health care fields from the selected first record in a second record of the second database;

a second processor operable via an executable application storable in a memory device to map a third record comprising a unique identifier and a plurality of health fields of a third database to the second record comprising the unique identifier and the plurality of health fields of the second database, whereby the third record is integrated with the second record, and whereby a combined database is provided, and the second processor operable to modify a health care practice to reduce correlation between the first health care field and the second health care field and review a result of a modified health care practice to validate health care costs, thereby normalizing health care costs;

an interface configured to: access the combined database; retrieve a plurality of combined records from the combined database; analyze the plurality of combined records by searching the plurality of health care fields- using a search engine and by filtering historical data according to a treatment type and a treatment stage, whereby an output of an analysis is provided; store the output in a health informatics database; and transmit the output;

an output interface configured to receive the output from the interface and to translate the output into at least one data format for displaying the output, the output comprising data from a first health care field overlaid on data from a second health care field; and a health informatics database configured to store the output.

12. The system according to claim 11, wherein the first processor is configured to receive the plurality of health care fields in a format comprising at least one data type of: DICOM, Non-DICOM, Video, Portable Document Format (PDF), Extensible Markup Language (XML), Audio, Image, and Text.

13. The system according to claim 11, wherein the interface for accessing the combined database comprises a remote interface.

14. The system according to claim 11, wherein the health informatics database is stored on at least one of: a local server, a cloud-based storage system, and a remote device.

15. The system according to claim 14, wherein the remote device comprises at least one of: a tablet, a smartphone, and a remote computer.

16. The system according to claim 11, wherein the combined data is displayed on the output interface.

17. The system according to claim 11, wherein the output interface comprises at least one of: a web-based application, a mobile device, and a computer terminal.

18. A system for storing and accessing medical records to relate health care data with health care costs and normalize health care costs, the system comprising:

a first database for storing a plurality of records, each record comprising a plurality of identification fields which, when collectively combined, identify an individual, and a plurality of health care fields corresponding to health care data associated with the individual, the plurality of health care fields comprising an information field and an intervention field associated with at least one of a cost field and a payer field, the information field comprising a diagnosis code, and the intervention field comprising a procedure code;

a second database;

a first processor in communication with the first and second database, the processor configured to: select a record from the first database, whereby a selected first record is provided;

assign a unique identifier based on the plurality of identification fields; and store the unique identifier and the plurality of health care fields from the first record in a second record of the second database;

a second processor operable via an executable application storable in a memory device, the second processor configured to map a third record comprising a unique identifier and a plurality of health fields of a third database to the second record comprising the unique identifier and the plurality of health fields of the second database, whereby the third record is integrated with the second record, whereby a combined database is provided, and the second processor operable to modify a health care practice to reduce correlation between the first health care field and the second health care field and review a result of a modified health care practice to validate health care costs;

an interface configured to: access the combined database; retrieve a plurality of combined records from the combined database; analyze the plurality of combined records by searching the plurality of health care fields- using a search engine and by filtering historical data according to a specific treatment type and a treatment stage, whereby an output of an analysis is provided; store the output in a health informatics database; and transmit the output;

an output interface to receive the output from the interface and to translate the output into at least one data format for displaying the output, the output comprising data from a first health care field overlaid on data from a second health care field; and a health informatics database to store the output.

* * * * *